(12) United States Patent
Hatzfeld et al.

(10) Patent No.: US 7,235,710 B2
(45) Date of Patent: Jun. 26, 2007

(54) REGULATORY SEQUENCE

(75) Inventors: Yves Hatzfeld, Lille (FR); Dirk Inze, Moorsel-Aalst (BE)

(73) Assignee: Cropdesign N.V., Zwijnaarde (BE)

( * ) Notice: Subject to any disclaimer, the term of this patent is extended or adjusted under 35 U.S.C. 154(b) by 0 days.

(21) Appl. No.: 10/541,315

(22) PCT Filed: Jan. 21, 2004

(86) PCT No.: PCT/EP2004/000645

§ 371 (c)(1),
(2), (4) Date: Jun. 30, 2005

(87) PCT Pub. No.: WO2004/065596

PCT Pub. Date: Aug. 5, 2004

(65) Prior Publication Data

US 2006/0053507 A1    Mar. 9, 2006

(30) Foreign Application Priority Data

Jan. 21, 2003    (EP)    ................... 03075207

(51) Int. Cl.
C12N 15/82    (2006.01)
C12N 5/04    (2006.01)
C12N 5/10    (2006.01)
A01H 5/00    (2006.01)

(52) U.S. Cl. ...................... 800/278; 435/415; 435/416; 435/417; 435/419; 435/468; 536/24.1; 800/295

(58) Field of Classification Search ..................... None
See application file for complete search history.

(56) References Cited

U.S. PATENT DOCUMENTS 6,066,456 A * 5/2000 Bridges et al. ................. 435/6

OTHER PUBLICATIONS

De Pater et al The promoter of the rice gene GOS2 is active in various different monocot tissues and binds rice nuclear factor ASF-1. The Plant Journal 1992 2:6 837.*
International Search Report for PCT/EP2004/000645 dated Aug. 19, 2004.
Pater et al., The Promoter of the Rice Gene GOS2 Is Active In Various Different Monocot Tissues and Binds Rice Nuclear Factor ASF-1, *Plant Journal*, vol. 2, No. 6, 1992, pp. 837-844, XP000907326.
Quellet et al., The wheat wcs120 promoter is cold-inducible in both monocotyledonous and dicotyledonous species, *FEBS Letters*, vol. 423, No. 3, Feb. 27, 1998, pp. 324-328, XP004261912.
Luan et al., A Rice Cab Gene Promoter Contains Separate CIS-acting Elements that Regulate Expression in Dicot and Monocot Plants, *Plant Cell*, vol. 4, No. 8, 1992, pp. 971-981, XP002283900.
Hauptmann et al., Promoter Strength Comparisons of Maize Shrunken 1 and Alcohol Dehydrogenase 1 and 2 Promoters in Monocotyledonous and Dicotyledonous Species, *Plant Physiology*, vol. 88, No. 4, 1988, pp. 1063-1066, XP001182033.
Database Biosis, Deng et al., *Expression of a zein gene Z4 introduced into dicotyledonous Solanum nigrum*, XP002283901.

* cited by examiner

*Primary Examiner*—David T. Fox
*Assistant Examiner*—Brendan O. Baggot
(74) *Attorney, Agent, or Firm*—Nixon & Vanderhye P.C.

(57) ABSTRACT

The present invention relates to the field of plant molecular biology. In particular, it describes the use of a regulatory nucleic acid sequence of the rice gene GOS2 for the regulation of gene expression in plant cells derived from plants other than monocotyledonous plants. The use of the regulatory sequence of the present invention results in constitutive expression with expression levels similar to that of CaMV 35S. The present invention also relates to vectors and host cells comprising these nucleic acid sequences. The invention further relates to transgenic cells and plants comprising these sequences and to methods for obtaining such cells and plants.

8 Claims, 5 Drawing Sheets

SEQUENCE LISTING

<160> NUMBER OF SEQ ID NOS: 3

<210> SEQ ID NO 1
<211> LENGTH: 2195
<212> TYPE: DNA
<213> ORGANISM: Oryza sativa

<400> SEQUENCE: 1

| | | | | |
|---|---|---|---|---|
| aatccgaaaa | gtttctgcac | cgttttcacg | tcctaactaa | caatataggg | aacgtgtgct | 60 |
| aaatataaaa | tgagacctta | tatatgtagc | gctgataact | agaactatgt | aagaaaaact | 120 |
| catccaccta | ctttagtggc | aatcgggcta | aataaaaaag | agtcgctaca | ctagtttcgt | 180 |
| tttccttagt | aattaagtgg | gaaaatgaaa | tcattattgc | ttagaatata | cgttcacatc | 240 |
| tctgtcatga | agttaaatta | ttcgaggtag | ccataattgt | catcaaactc | ttcttgaata | 300 |
| aaaaaatctt | tctagctgaa | ctcaatgggt | aaagagagat | attttttttt | aaaaaaaaat | 360 |
| agaatgaaga | tattctgaac | gtatcggcaa | agatttaaac | atataattat | ataattttat | 420 |
| agtttgtgca | ttcgttatat | cgcacgtcat | taaggacatg | tcttactcca | tctcaatttt | 480 |
| tatttagtaa | ttaaagacaa | ttgacttatt | tttattattt | atcttttttc | gattagatgc | 540 |
| aaggtactta | cgcacacact | ttgtgctcat | gtgcatgtgt | gagtgcacct | cctcatacac | 600 |
| gttcaactag | cgacacatct | ccaatatcac | tcgcctattt | aatacattta | ggtagcaata | 660 |
| tctgaattca | agcacttcac | catcaccaga | ccacttttaa | taatatctaa | aatacaaaaa | 720 |
| ataattttac | agaatagcat | gaaaagtatg | aaacgaacta | tttaggtttt | tcacatacaa | 780 |
| aaaaaaaaag | aattttgctc | gtgcgcgagc | gccaatctcc | catattgggc | acacaggcaa | 840 |
| caacagagtg | gctgcccaca | gaacaaccca | caaaaaacga | tgatctaacg | gaggacagca | 900 |
| agtccgcaac | aaccttttaa | cagcaggctt | tgcggccagg | agagaggagg | agaggcaaag | 960 |
| aaaaccaagc | atcctcctcc | tcccatctat | aaattcctcc | cccttttcc | cctctctata | 1020 |
| taggaggcat | ccaagccaag | aagagggaga | gcaccaagga | cacgcgacta | gcagaagccg | 1080 |
| agcgaccgcc | ttcttcgatc | catatcttcc | ggtcgagttc | ttggtcgatc | tcttccctcc | 1140 |
| tccacctcct | cctcacaggg | tatgtgccct | tcggttgttc | ttggatttat | tgttctaggt | 1200 |
| tgtgtagtac | gggcgttgat | gttaggaaag | gggatctgta | tctgtgatga | ttcctgttct | 1260 |
| tggatttggg | atagaggggt | tcttgatgtt | gcatgttatc | ggttcggttt | gattagtagt | 1320 |
| atggttttca | atcgtctgga | gagctctatg | gaaatgaaat | ggtttagggt | acggaatctt | 1380 |
| gcgattttgt | gagtaccttt | tgtttgaggt | aaaatcagag | caccggtgat | tttgcttggt | 1440 |
| gtaataaaag | tacatttgtt | tggtcctcga | ttctggtagt | gatgcttctc | gatttgacga | 1500 |
| agctatcctt | tgtttattcc | ctattgaaca | aaaataatcc | aactttgaag | acggtcccgt | 1560 |
| tgatgagatt | gaatgattga | ttcttaagcc | tgtccaaaat | ttcgcagctg | gcttgtttag | 1620 |
| atacagtagt | ccccatcacg | aaattcatga | aaacagttat | aatcctcagg | aacaggggat | 1680 |
| tccctgttct | tccgatttgc | tttagtccca | gaattttttt | tcccaaatat | cttaaaaagt | 1740 |
| cactttctgg | ttcagttcaa | tgaattgatt | gctacaaata | atgcttttat | agcgttatcc | 1800 |
| tagctgtagt | tcagtttata | ggtaataccc | ctatagttta | gtcaggagaa | gaacttatcc | 1860 |
| gatttctgat | ctccattttt | aattatatga | aatgaactgt | agcataagca | gtattcattt | 1920 |
| ggattatttt | ttttattagc | tttcacccct | tcattattct | gagctgaaag | tctggcatga | 1980 |
| actgtcctca | attttgtttt | caaattcaca | tcgattatct | atcgattatc | ctcttgtatc | 2040 |

```
tacctgtaga agtttctttt tggttattcc ttgactgctt gattacagaa agaaatttat        2100
gaagctgtaa tcgggatagt tatactgctt gttcttatga ttcatttcct ttgtgcagtt        2160
cttggtgtag cttgccactt tcaccagcaa agttc                                  2195

<210> SEQ ID NO 2
<211> LENGTH: 61
<212> TYPE: DNA
<213> ORGANISM: Artificial sequence
<220> FEATURE:
<223> OTHER INFORMATION: sense primer attB1

<400> SEQUENCE: 2
ggggacaagt ttgtacaaaa aagcaggctt cacaatgtta cgtcctgtag aaaccccaac        60
c                                                                        61

<210> SEQ ID NO 3
<211> LENGTH: 52
<212> TYPE: DNA
<213> ORGANISM: Artificial sequence
<220> FEATURE:
<223> OTHER INFORMATION: antisense primer attB2

<400> SEQUENCE: 3
ggggaccact ttgtacaaga aagctgggtt tgttgattca ttgtttgcct cc                52
```

REGULATORY SEQUENCE

This application is the US national phase of international application PCT/EP2004/000645 filed 21 Jan. 2004, which designated the U.S. and claims benefit of EP 03075207.5 filed 21 Jan. 2003, the entire contents of each of which are hereby incoroorated by reference.

The present invention relates to the field of plant molecular biology. In particular, the present invention describes the use of a regulatory sequence of the rice GOS2 gene for the regulation of gene expression in plant cells of non-monocotyledonous plants.

Plant genetic engineering has the potential to enable the production of plants having all manner of desirable traits, such as increased pathogen resistance, herbicide resistance, increased yield, increased stress tolerance etc. This is typically achieved by inserting suitable pieces of DNA from a heterologous source, or from the same source, into a plant. The expression of heterologous DNA sequences in a plant host is dependent upon the presence of an operably linked promoter that is functional within the plant host.

Promoters are DNA elements that regulate transcription in prokaryotic and eukaryotic cells, and are located in the 5'-flanking or upstream region of a transcribed gene. The sequence of a promoter varies in length and base pair composition from gene to gene. Many regulatory sequence elements may be present within the sequence of a promoter. These regulatory sequence elements, which interact with DNA binding proteins (that are part of the transcription initiation complex) are generally embedded in a promoter sequence. Specific elements, called DNA-boxes, contribute defined features or a defined activation pattern to a promoter. Many of these boxes are recognition sites to which regulatory transcription factors can bind and are part of a tight control mechanism of the promoter. Numerous plant promoter DNA boxes have been described, such as tissue-specific boxes (Chaubet et al., Plant J. 10 (3) 425–435, 1996), pyrimidin boxes (Gubler & Jacobsen, Plant Cell 4 (11) 1435–1441, 1992) which influence the level of expression, or G-boxes (Dolferus et al, Plant Physiol. 105 (4) 1075–1087, 1994), which reduce promoter activity upon exposure to cold or dehydration.

Recombinant DNA technology has now found a wide application in research and in product development. In molecular biology, specific types of promoters are frequently used for the expression of heterologous nucleic acids or proteins in organisms, in which the expression may be constitutive (i.e. continuous expression throughout the cells of an organism), or limited to defined parts of an organism (i.e. tissue or cell preferred expression), or limited to certain developmental stages or to certain environmental or physiological conditions (i.e. inducible expression).

A need exists in various industrial applications for transcriptional control elements capable of driving gene-expression in plants. Therefore, in order to obtain desired gene expression, which can be fine tuned depending on specific needs, it is desirable to provide a wide array of promoters from which one can be chosen. Persons skilled in the art need to have at their disposal a variety of promoters with different expression patterns or with different time-control features from which to choose. For many industrial and agronomic applications, where the aim is to confer a given characteristic throughout plant development and during any environmental or physical state of the plant, a constitutive promoter would be needed. A constitutive promoter may be suitable for driving expression of selectable marker genes or may be used when the gene product of a particular gene is to be isolated and purified from the plant for commercial purposes.

It is also frequently desirable to use promoters that are regulated in a comparable way to each other and result in a similar expression pattern over a wide range of host species. Very few constitutive plant promoters that are active in a wide range of species have been isolated to date (Callis et al., J. Biol. Chem. 265 12486–12493, 1990; Zhang et al., Plant Cell 3 1155–1165, 1991; de Pater et al., Plant J. 2 837–844, 1992; Mandel et al. Plant Mol. Biol. 29 995–1004, 1995; Baszczynski et al., Maydica 42 189–201, 1997). As a result, the cauliflower mosaic virus 35S (CaMV 35S; Odell et al., Nature 313 653–660, 1985) is currently the most widely used constitutive promoter in plant science. Its regulation is well known and it has been shown to work in many monocotyledonous and dicotyledonous plant species, and even in some fungal species. The main drawback of such a promoter however is its viral origin. Plants transformed with the CaMV35S promoter frequently show several undesirable characteristics, such as efficient silencing of the transgenes or increased recombination, leading to instability over time and over subsequent generations (Kohli et al., Plant J. 17 591–601, 1999; Al-Kaff et al., Nature Biotechnology 18 995–999, 2000). In addition, viral elements are often not desirable in transgenic products, both for regulatory reasons and for reasons of general public acceptance.

Rice GOS2 cDNA was isolated and characterised in a screening program for genes that were expressed in many different rice tissues (de Pater et al., Plant J. 2, 837–844, 1992). GOS2 is a single copy gene that encodes an isoform of the translation initiation factor eIF1. Expression analysis revealed high mRNA levels in green shoots, etiolated shoots and in roots of seedlings. A similar expression pattern was detected in mature plants, though the expression was a bit lower in roots. High expression levels were also detected in plants or cell suspension cultures of another rice variety. An isolated promoter fragment was able to drive GUS expression in rice seedlings (leaf, root tissues and coleoptile), and in rice cell suspension cultures. The promoter was also active in maize, barley and ryegrass (de Pater et al., Plant J. 2, 837–844, 1992; Hensgens et al., Plant Mol. Biol. 22, 1101–1127, 1993). It has been shown to be active in other monocotyledonous plants, with expression levels similar to that of CaMV 35S. Barbour et al. (WO0020571) suggest, but did not show, the use of a GOS2 promoter from maize in dicotyledonous plants. There is however little homology between the maize GOS2 promoter and the rice GOS2 promoter that is the subject of the present invention.

It has now been found that a GOS2 regulatory sequence from rice is active in non-monocotyledonous plants, and has a similar expression pattern and strength to the CaMV 35S promoter. Consequently, the present invention concerns the use of a GOS2 regulatory sequence for driving constitutive expression of nucleic acids in non-monocotyledonous plants. The present invention therefore provides a good alternative for the CaMV 35S promoter. The regulatory sequence of the present invention, when linked to a useful gene and transferred into a non-monocotyledonous plant or plant cell, enables expression of that useful gene. In addition, since the regulatory sequence of the present invention enables constitutive expression, it is possible to use it as a regulatory sequence to drive expression of the transferred useful gene in all tissues at any developmental stage. Moreover, as this regulatory sequence originates from a monocotyledonous plant, it is less likely to be prone to silencing than dicotyledonous regulatory sequence or the CaMV35S promoter, when used to express a transferred useful gene in dicotyledonous plants, such as *Arabidopsis thaliana*.

Those skilled in the art will be aware that the invention described-herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of these steps or features.

Throughout this specification, unless the context requires otherwise, the word "comprise", and variations such as "comprises" and "comprising", will be understood to imply the inclusion of a stated integer or step or group of integers or steps but not to the exclusion of any other integer or step or group of integers or steps.

As used herein, the term "derived from" shall be taken to indicate that a particular integer or group of integers has originated from the species specified, but has not necessarily been obtained directly from the specified source. This integer may be substantially modified from its native form in composition and/or environment through deliberate human manipulation.

In accordance with the present invention, there is provided the use of an isolated regulatory nucleic acid sequence comprising a regulatory sequence as represented by SEQ ID NO 1 or by a functional fragment or functional variant thereof, for driving expression of an associated nucleic acid sequence in a non-monocotyledonous plant or plant cell.

The term "regulatory sequence" as used herein refer to DNA sequences which are necessary to effect expression of sequences to which they are ligated. The regulatory sequences may differ depending upon the intended host organism and upon the nature of the sequence to be expressed. The term "regulatory sequence" is intended to include, as a minimum, all components necessary for expression and optionally additional advantageous components. According to a preferred feature, the isolated regulatory nucleic acid sequence is a promoter sequence. As used herein, a 'promoter' means a region of DNA upstream from the transcription start and which is involved in binding RNA polymerase and other proteins to start transcription. Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. Consequently, a repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions. The term "promoter" also includes the transcriptional regulatory sequences of a classical prokaryotic gene, in which case it may include a -35 box sequence and/or a -10 box transcriptional regulatory sequences. The term "promoter" is also used to describe a synthetic or fusion molecule, or derivative which confers, activates or enhances expression of a nucleic acid molecule in a cell, tissue or organ.

The present invention thus also encompasses the use of fragments or variants of SEQ ID NO 1, which may be joined by any means known in the art, e.g., by ligation in vitro, to create hybrid regulatory sequences comprising mixtures of parts of regulatory elements from different sources, either natural or synthetic. Therefore, the invention also provides a hybrid regulatory nucleic acid sequence comprising the regulatory sequence represented by SEQ ID NO 1 or a fragment or variant thereof, functionally combined with one or more other regulatory sequences or fragments thereof.

Regulatory sequences or promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid, or to confer expression of a nucleic acid molecule to specific cells, tissues or organs such as meristems, leaves, roots, embryo, flowers, seeds or fruits. In the context of the present invention, the regulatory sequence is active in non-monocotyledonous plants, and is represented by SEQ ID NO1, a functional fragment or a functional variant thereof. The term "functional", when used in respect of a nucleic acid or part thereof, is to be understood as having an essentially similar biological activity compared to the naturally occurring nucleic acid and being capable of driving expression in non-monocotyledonous plants.

"Expression" means the production of a protein or nucleotide sequence in a cell itself or in a cell-free system. It includes transcription into an RNA product, post-transcriptional modification and/or translation to a protein product or polypeptide from a DNA encoding that product, as well as possible post-translational modifications. A coding sequence can be transcribed in sense or antisense direction.

The term "nucleic acid sequence(s)", "nucleic acid molecule(s)", "polynucleotide(s)", "nucleotide sequence(s)", "DNA sequence(s)" or "gene(s)", when used herein refers to nucleotides, either ribonucleotides (RNA) or deoxyribonucleotides (DNA) or a combination of both, in a polymeric form of any length. These terms furthermore include double-stranded and single-stranded DNA and RNA. These terms also include nucleotide modifications known in the art, such as methylation, cyclisation, 'caps', substitution of one or more of the naturally occurring nucleotides with an analogue such as inosine, and polynucleotide backbone modifications. The term "isolated" in the present application means removed from its original environment. For example, a nucleic acid present in the natural state in an organism is not isolated, whereas the same nucleic acid separated from the adjacent nucleic acids in which it is naturally present, is regarded as being "isolated".

An associated nucleic acid sequence may comprise coding sequences or it may contain non-coding sequences. A "coding sequence" or "open reading frame" or "ORF" is defined as a nucleotide sequence that can be transcribed into mRNA and/or translated into a polypeptide when placed under the control of appropriate regulatory sequences, i.e. when the coding sequence or ORF is present in an expressible form. The coding sequence or ORF is bound by a 5' translation start codon and a 3' translation stop codon. A coding sequence or ORF may include, but is not limited to RNA, mRNA, cDNA, recombinant nucleotide sequences, synthetically manufactured nucleotide sequences or genomic DNA. The coding sequence or ORF can be interrupted by intervening nucleic acid sequences.

Coding sequences, or genes essentially encoding the same protein but isolated from different sources, can consist of substantially divergent nucleic acid sequences. Reciprocally, substantially divergent nucleic acid sequences can be designed to effect expression of essentially the same protein. These nucleic acid sequences are the result of e.g. the existence of different alleles of a given gene, or of the degeneracy of the genetic code or of differences in codon usage. Thus, amino acids such as methionine and tryptophan are encoded by a single codon whereas other amino acids such as arginine, leucine and serine can each be translated from up to six different codons. Preferred codon usage of various organisms can be found on the internet at URL: kazusa.or.jp/codon. Allelic variants are further defined as comprising single nucleotide polymorphisms (SNPs) as well as small insertion/deletion polymorphisms (INDELs; the size of INDELs is usually less than 100 bp). SNPs and INDELs form the largest set of sequence variants in naturally occurring polymorphic strains of most organisms.

The term "associated" as used herein, or "operably linked" refers to a juxtaposition between a regulatory and a coding sequence, wherein the components so described are in a relationship permitting them to function in their intended manner. A regulatory sequence "operably linked" to a coding sequence is ligated in such a way that expression of the coding sequence is achieved under conditions compatible with the control sequences. In case the regulatory sequence is a promoter, it would be known to a skilled person that a double-stranded nucleic acid is preferable. The associated nucleic acid encompasses heterologous nucleic acids. Heterologous nucleic acids refer to nucleic acids derived from a separate genetic source, for example nucleic acids that originate from within the cell but that are not naturally located in the cell, or that are located in a different chromosomal site of the cell. Heterologous nucleic acids may also be derived from other species and may be introduced as a transgene, for example, by transformation. This transgene may be substantially modified from its native form in composition and/or genomic environment through deliberate human manipulation. Also expression of the native nucleic acid sequences may be modified by introduction in the plant of regulatory sequences according to the invention in such a way that the regulatory sequences are operably linked to the native nucleic acid. Native nucleic acid refer to nucleic acid in their natural location in the genome of an organism.

The term "fragment of a sequence" or "part of a sequence" means a truncated sequence of the original sequence in question. The truncated nucleic acid sequence can vary widely in length; the minimum size being a sequence of sufficient size to provide a sequence with at least a comparable function and/or activity of the original sequence in question, while the maximum size is not critical. In some applications, the maximum size usually is not substantially greater than that required to provide the desired activity and/or function(s) of the original sequence. These terms are not restrictive to the content of the DNA fragment or segment, which can be any DNA, with any functionality. For example the DNA fragment or segments may consist of a promoter but may also comprise many genes, with or without additional control elements, it may just contain spacer sequences. A functional fragment of a promoter may be constructed by deleting parts at the 5' and/or 3' end, and/or by deleting internal parts and testing the remaining fragment for its ability to drive expression of a reporter gene. The expression level and pattern of this reporter gene construct can then be compared to that of the same reporter gene under control of the original promoter from which the fragment was derived.

Furthermore, a variant of a DNA fragment encompasses a sequence showing homology to the sequence referred to and is capable of promoting expression of an associated DNA sequence when reintroduced into a plant and hybridises to the sequence referred to or to a portion thereof under stringent conditions. The person skilled in the art will appreciate that in this case, reactions under stringent conditions for hybridisation are typically carried out at a temperature of between 60° C. and 65° C. in 0.3 strength citrate buffer saline containing 0.1% SDS followed by rinsing at the same temperature with 0.3 strength citrate buffer saline containing 0.1% SDS. For the purposes of defining the level of stringency, reference can conveniently be made to Sambrook et al. (2001) Molecular Cloning: a laboratory manual, 3rd Edition Cold Spring Harbor Laboratory Press, CSH, New York or to Current Protocols in Molecular Biology, John Wiley & Sons, N.Y. (1989).

A "non-monocotyledonous plant" comprises all plant species which belong to the kingdom Plantae as defined by ITIS [the Integrated Taxonomic Information System (internet URL: itis.usda.gov/index.html], including the class of Magnoliopsida but without the class of the Liliopsida (Liliatae, Monocotyledonae), The classes Magnoliopsida and Liliopsida are part of the division Magnoliophyta, which in turn belongs to the subkingdom Tracheobionta. The isolated nucleic acid according to the present invention can be used to drive gene expression in any non-monocotyledonous plant, in particular it is applicable to a dicotyledonous plant including a fodder or forage legume, ornamental plant, food crop, tree, or shrub. Preferred plant species include cotton, potato, tomato, cabbage, sugar beet, soybean, bean, sunflower, peas.

Advantageously, the regulatory sequence represented by SEQ ID NO 1 or a functional fragment or functional variant thereof is capable of driving expression of an associated nucleic acid sequence in a non-monocotyledonous plant. Such an associated nucleic acid may be any heterologous DNA sequence derived from any organism which sequence is to be expressed in a non-monocotyledonous plant. The heterologous DNA sequence may be obtained from any organism, including plants, which plant species may be the same plant species into which the sequence is to be introduced, or it may be different. Additionally or alternatively, the associated nucleic acid sequence may be an endogenous nucleic acid operably linked to the regulatory sequence according to the invention.

Therefore, the invention also provides use of an isolated regulatory nucleic acid as defined above for driving expression of an associated nucleic acid in a non-monocotyledonous plant or plant cell, wherein said associated nucleic acid is an isolated nucleic acid or a nucleic acid endogenous to the host cell in which said isolated regulatory nucleic acid sequence is introduced.

The recombinant nucleic acid encompasses any means for the cloning of and/or transfer of a nucleic acid into a host cell, including "vectors" or "vector sequences", which may be introduced in an organism by transformation or transfection, and which may either be integrated into the genome of the host cell or maintained in some form extrachromosomally. Vector sequences generally comprise a set of unique sites recognised by restriction enzymes, the multiple cloning site (MCS), wherein one or more non-vector sequence(s) can be inserted.

With "non-vector sequence" or "insert" is accordingly meant the desired DNA segment which one wishes to clone in one or more of the sites of the MCS, comprised within a vector. The insert can have one or more genes.

"Expression vectors" form a subset of vectors, which, by virtue of comprising the appropriate regulatory sequences enabling the creation of an expressible format for the inserted non-vector sequence(s), thus allowing transcription and/or translation of a nucleic acid inserted therein. Expression vectors are known in the art and enable protein expression in organisms including bacteria (e.g. *Escherichia coli*), fungi (e.g. *Saccharomyces cerevisiae, Schizosaccharomyces pombe, Pichia pastoris*), insect cells (e.g. baculoviral expression vectors), animal cells (e.g. COS or CHO cells) and plant cells (e.g. potato virus X-based expression vectors, see e.g. Vance et al. 1998—WO9844097). Expression vectors can for instance be cloning vectors, binary vectors or integrating vectors.

Regulatory sequences ensuring expression in prokaryotic and/or eukaryotic cells, particularly in non-monocotyledonous plants, are well known to those skilled in the art. A preferred regulatory sequence is the regulatory sequence listed in SEQ ID NO 1, a functional fragment or a functional variant thereof. When used in eukaryotic cells vectors may also comprise terminators which contain polyadenylation signals ensuring 3' processing and polyadenylation of a primary transcript and termination of transcription. In plant cells the termination signals usually employed are from the nopaline synthase gene or the CaMV 35S terminator. Additional regulatory elements may include transcriptional as well as translational enhancers. A plant translational enhancer often used is the CaMV omega sequence. The inclusion of an intron has been shown to increase expression levels by up to 100-fold in certain plants (Maiti et al., Transgenic Research 6 143–156, 1997; Ni, Plant Journal 7 (1995), 661–676).

Advantageously, vectors used in the invention comprise a selectable and/or scorable marker. Selectable marker genes useful for the selection of transformed plant cells, callus, plant tissue and plants are well known to those skilled in the art. Antimetabolite resistance is very useful as a basis for selection: for example, the dhfr gene confers resistance to methotrexate (Reiss et al., Plant Physiol. (Life Sci. Adv.) 13 143–149, 1994); the npt gene confers resistance to the aminoglycosides neomycin, kanamycin and paromomycin (Herrera-Estrella et al., EMBO J. 2 987–995, 1983); or the hpt gene, which confers resistance to hygromycin (Marsh, Gene 32 481–485, 1984). Additional selectable markers genes have been described, such as trpB, which allows cells to utilize indole in place of tryptophan; hisD, allowing cells to utilize histinol in place of histidine (Hartman, Proc. Natl. Acad. Sci. USA 85 8047, 1988); mannose-6-phosphate isomerase enabling cells to utilize mannose (WO 94/20627) and ornithine decarboxylase which confers resistance to the ornithine decarboxylase inhibitor, 2-(difluoromethyl)-DL-ornithine or DFMO (McConlogue, 1987, In: Current Communications in Molecular Biology, Cold Spring Harbor Laboratory ed.) or the deaminase gene from *Aspergillus terreus* which confers resistance to Blasticidin S (Tamura, Biosci. Biotechnol. Biochem. 59 2336–2338, 1995). Useful scorable markers are also known to those skilled in the art and are commercially available. Advantageously, the marker is a gene encoding luciferase (Giacomin, Pl. Sci. 116 59–72, 1996; Srikantha, J. Bact. 178 121, 1996), green fluorescent protein (Gerdes, FEBS Lett. 389 44–47, 1996; Haseloff et al., Proc. Natl. Acad. Sci U.S.A. 94 2122–2127, 1997) or β-glucuronidase (Jefferson, EMBO J. 6 3901–3907, 1987).

Vectors may further provide primer sites, e.g., for PCR, transcriptional and/or translational initiation and/or regulation sites, recombinational sites, replicons, etc.

The current invention clearly includes any recombinant nucleic acid, vector or expression vector comprising the regulatory sequence according to the present invention and/or a non-vector sequence as defined supra.

According to another embodiment, the invention relates to a non-monocotyledonous plant cell comprising a recombinant nucleic acid as described above. The recombinant nucleic acid may be stably integrated into the genome of the non-monocotyledonous plant cell. The invention also provides a plant cell culture, callus, a plant or a plant part derived from these plant cells. Also within the scope of the present invention is a harvestable part, organ, tissue or propagation material of a plant according to the invention, comprising a nucleic acid sequence comprising a regulatory sequence represented by SEQ ID NO: 1 or a fragment or variant thereof.

Furthermore, there is provided a method for expression of a nucleic acid sequence in a non-monocotyledonous plant cell, which method comprises introducing into this plant cell a regulatory sequence represented by SEQ ID NO 1 or a functional fragment or functional variant thereof, wherein the regulatory sequence is capable of driving expression of the nucleic acid sequence which is either an isolated or endogenous nucleic acid sequence.

Means for introducing recombinant DNA into plant tissue or cells include, but are not limited to, transformation using $CaCl_2$ and variations thereof (Hanahan, J. Mol. Biol. 166 (4) 557–580, 1983)), direct DNA uptake into protoplasts (Krens et al., Nature 296 72–74, 1982; Paszkowski et al., EMBO J. 3 2717–2722, 1984), PEG-mediated uptake to protoplasts (Armstrong et al., Plant Cell Reports 9 335–339, 1990) microparticle bombardment, electroporation (Fromm et al., Proc. Natl. Acad. Sci. U.S.A. 82 5824–5826, 1985) microinjection of DNA (Crossway et al., Mol. Gen. Gen. 202 179–185, 1986; Fromm et al. Proc. Natl. Acad. Sci. U.S.A. 82 5824–5826, 1985), microparticle bombardment of tissue explants or cells (Christou et al., Plant Physiol. 87 671–674, 1988), vacuum-infiltration of tissue with nucleic acid, or in the case of plants, T-DNA-mediated transfer from *Agrobacterium* to the plant tissue as described essentially (An et al., EMBO J. 4 277–284, 1985; Dodds, Plant genetic engineering, 1985; Herrera-Estrella et al., EMBO J. 2 987–995, 1983; Herrera-Estrella et al., Nature 303 209–213, 1983).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation, The nucleic acid as defined above in the present invention, or a genetic construct comprising it, may be introduced into a cell using any known method for the transfection or transformation.

The invention further relates to a method for the production of non-monocotyledonous transgenic plants, plant cells or plant tissues comprising the introduction in a non-monocotyledonous plant, plant cell or plant tissue of a first nucleic acid molecule according to the invention operably linked to an associated nucleic acid sequence, wherein the associated nucleic acid sequence is heterologous to the first nucleic acid. According to another preferred embodiment, the invention relates to a non-monocotyledonous transgenic plant cell or plant as described here above wherein the nucleic acid of the invention is stably integrated into the genome of the non-monocotyledonous plant cell or plant.

Upon transformation of a cell with the genetic construct of the invention, a whole plant may be regenerated therefrom. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The term "organogenesis", as used herein, means a process by which shoots and roots are developed sequentially from meristematic centres. The term "embryogenesis", as used herein, means a process by which shoots and roots develop together in a concerted fashion (not sequentially), whether from somatic cells or gametes.

The generated transformed non-monocotyledonous plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques. The generated transformed plants contemplated herein may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The invention not only relates to a transgenic non-monocotyledonous plant or plant tissue comprising plant cells as herein described but extends also to the harvestable parts of the transgenic plant, preferably selected from the group consisting of seeds, leaves, flowers, fruits, stem cultures, roots, tubers, rhizomes and bulbs. The invention also relates to the progeny derived from any of these transgenic plants or plant parts.

The present invention also encompasses use of an isolated nucleic acid sequence comprising a regulatory sequence as represented by SEQ ID NO 1 or a functional fragment or functional variant thereof, characterised as above for driving constitutive expression of an associated sequence in a non-monocotyledonous plant cell or plant. Also included is the use of a hybrid regulatory nucleic acid as defined above for driving expression of an associated nucleic acid sequence in a non-monocotyledonous plant cell or plant.

EXAMPLES

Figure 1:
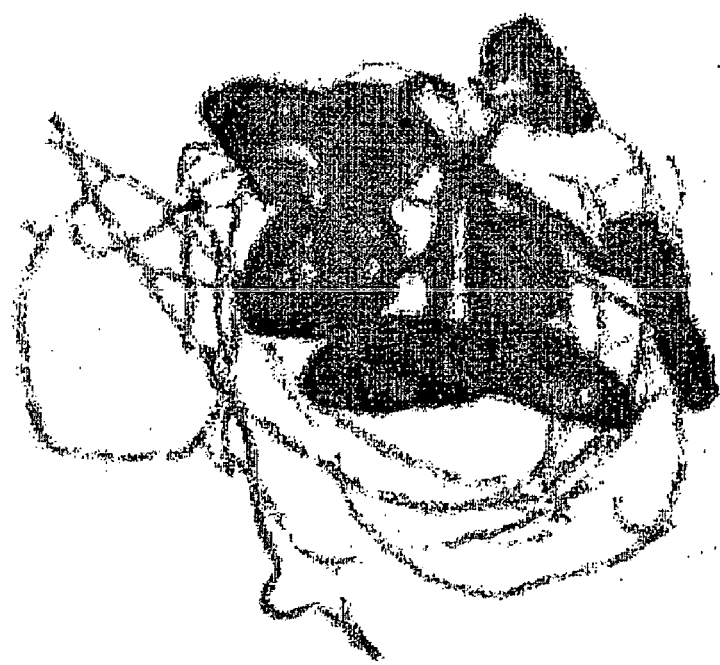
FIG. 1: Typical GUS expression pattern in an *Arabidopsis thaliana* plant transformed with a p2203 construct and a control plant. The GOS2 regulatory sequence shows a strong constitutive expression in shoot tissues, including the petioles, the vascular system, trichomes and in root tips. Expression in other root tissues is lower, but still easily noticeable.
Figure 1:

The present invention will now be illustrated with the following examples.

DNA Manipulation

All DNA procedures were performed according to standard protocols (Maniatis T et al. (2001). Molecular Cloning: a laboratory manual, Cold Spring Harbor Laboratory Press, CSH, New York).

Example 1

Cloning of GUS with Intron Coding Sequence

The *E. coli* β-glucuronidase gene, interrupted by the second intron of the Potato light-inducible tissue-specific ST-LS1 gene, was amplified from vector pTHW136 (with a cassette identical to the one of pMOG553, MOGEN international n.v, LEIDEN, NETHERLANDS). The cDNA was amplified by PCR with Platinum Pfx DNA polymerase (Invitrogen) and using a sense primer including attB1 (SEQ ID NO2) and an antisense primer including attB2 (SEQ ID NO3).

Conditions for PCR were: 2 minutes of denaturation at 94° C. (1 cycle); 35 cycles of 1 minute denaturation at 94° C., 1 minute annealing at 58° C. and 2 minutes amplification at 68° C., and finally 1 cycle of 5 minutes elongation at 68° C. A prominent fragment with the expected size of 2 kb was isolated from gel and purified using the Zymoclean Gel DNA Recovery Kit (Zymo Research, Orange, Calif.).

The purified PCR fragment was used in a standard Gateway™ BP reaction (Invitrogen) with pDONR201 as a recipient vector. The identity and base pair composition of the insert was confirmed by sequencing. The integrity of the resulting plasmid was verified using restriction digests and was given the designation p0604 (entry clone). pDONR201 was obtained from Invitrogen.

p0604 is a Gateway™ "entry clone", and was used as such in a standard Gateway™ LR reaction, with p0640 as "destination vector". The resulting vector was p02203, its integrity was also checked by restriction digest analysis. The vector, containing as functional elements within the T-DNA region a selectable marker gene and a "Gateway cassette" intended for LR cloning of sequences of interest, was used for the transformation of *Arabidopsis thaliana*. Expression of these sequences of interest, upon being recombined into p0640, was driven by the regulatory sequence as listed in SEQ ID NO1.

Example 2

Transformation of Plants

Cultivation of the Parental Plants

For the parental plants, approximately 12 mg of wild-type *Arabidopsis thaliana* (ecotype Columbia) seeds were suspended in 27.5 ml of 0.2% agar solution. The seeds were incubated for 2 to 3 days at a temperature of 4° C. and then sown. The plants were germinated under standardised conditions: 22° C. during the day, 18° C. at night, with a relative humidity of 65–70%, 12 hours of photoperiod and sub-irrigation with water for 15 min every 2 or 3 days. The seedlings were then transplanted into pots with a diameter of 5.5 cm, containing a mixture of sand and peat in a ratio of 1 to 3. The plants were then further grown under the same standard conditions as mentioned above.

*Agrobacterium* Growth Conditions and Preparation

*Agrobacterium* strain C58C1RIF with helper plasmid pMP90 and vector p2203 was inoculated in a 50 ml plastic tube containing 1 ml LB (Luria-Bertani Broth) without antibiotic. The culture was shaken for 8–9 h at 28° C. Next, 10 ml of LB without antibiotic was added to the plastic tube and shaken overnight at 28° C. Following this, the OD at 600 nm was measured. At an optical density of approximately 2.0, 40 ml of 10% sucrose and 0.05% Silwet L-77 (a mixture of 84% polyalkyleneoxide modified heptamethyltrisiloxane and 16% allyloxypolyethyleneglycol methyl ether, OSI Specialties Inc) was added to the culture. The *Agrobacterium* culture thus obtained was used to transform the grown plants.

Flower Dip

When each parental flower had one inflorescence of 7–10 cm in height, the inflorescences were submerged in the *Agrobacterium* culture and swirled gently for 2–3 seconds. For each transformation, 2 plants were used. Hereafter, the plants were returned to the growing conditions as described above.

Seed Collection 5 weeks after the flowers were dipped in the *Agrobacterium* culture, watering of the plants was stopped. The plants were further incubated at 25° C. with a photoperiod of 20 hours. One week later, the seeds were harvested and placed in a seed drier during one week. The seeds were then cleaned, collected in 15 ml plastic tubes and stored at 4° C. until further processing.

T1 Seeds Generation

Transgenic T0 seeds were selected for their marker expression, and germinated. Plants were grown as described above, until T1 seeds were harvested. The different lines were given the name AT0476-xx, where xx is a number.

Example 3

Comparison of the GOS2 Regulatory Sequence and the 35S Promoter in *Arabidopsis*:

The expression pattern of the β-glucuronidase gene and strength of the GOS2 regulatory sequence were compared with those of the 35S promoter in *Arabidopsis*.

Plant Material Used:

AT0476-11: cassette GOS2 -GUS and screenable marker cassette (vector p2203) (T1 seeds) AT0476-09: cassette GOS2-GUS and screenable marker cassette (vector p2203) (T1 seeds) WS35S:GUS: cassette 35S-GUS, no marker selection, homozygous line from Versailles (T2 homozygous seeds), Wassilewskija (WS) background.

Procedure:

Around 100 seeds, after being kept at a temperature of 4° C. for at least 2 days, were sown in soil and the plants were cultivated under standard conditions: 22° C. during the day, 18° C. at night, 65–70% relative humidity, 12 hours of photoperiod, sub-irrigation with water for 15 min every 2 or 3 days.

When the plants had 2 cotyledons and 2 true leaves, marker expression in AT0476 lines was monitored and plants with a uniform marker expression pattern were retained.

Next, 10 plants of each GOS2 or 35S lines were carefully isolated from the soil and labelled for identification. 5 of the plants were stained for GUS during 1 hour, the other 5 plants were stained overnight. The short staining time was needed to assess qualitatively the relative strength of the promoters. If the staining reaction was saturated in less than 1 hour, the incubation time is to be reduced. In case the staining was very faint blue after one hour, the incubation time may be increased to 2–3 hours. Finally, the stained plants were photographed. For each line, 20 other plants were carefully isolated from the soil and transferred in individual small pots for further cultivation. When the plants had reached the 10-leaf stage, again 10 plants of each line were isolated, labelled and stained as described above. The stained plants were photographed. At flowering time, 10 plants per line with siliques in various maturation stages were isolated and processed as above.

Plant GUS Staining Procedure

The material was covered with 90% ice-cold acetone and incubated for 30 min at 4° C. After 3 washes of 5 minutes with Tris buffer [15.76 g Trizma HCl (Sigma T3253)+2.922 g NaCl in 1 l double distilled water, adjusted pH to 7.0 with NaOH], the material was immersed in a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 µl DMSO)]. Vacuum infiltration was applied for 15 to 30 minutes. Next, the samples were incubated for an appropriate time (up to 16 hours) at 37° C. for development of the blue colour. The samples were washed 3 times during 5 minutes with Tris buffer. Chlorophyll was extracted in a series of 50%, 70% and 90% ethanol (each for 30 minutes) with refreshments of the 90% solution if necessary.

Results

The GOS2 regulatory sequence shows a strong constitutive expression in shoot tissues, including the petioles, the vascular system and trichomes. Except for the root tips, the expression in root tissues is lower, but is still easily detectable (FIG. 1).

Figure 2:
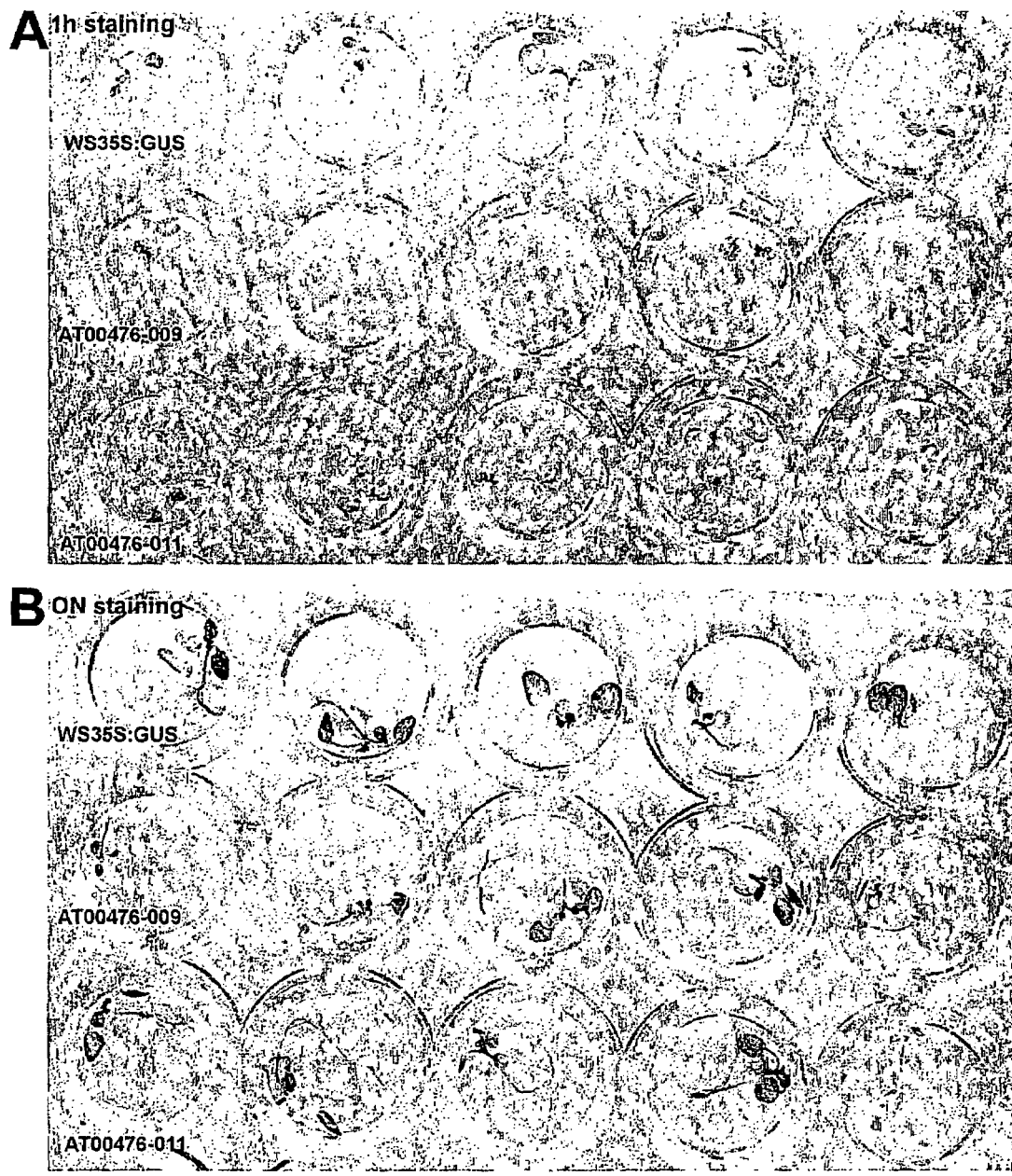
FIG. 2: GUS expression under control of the GOS2 regulatory sequence (lines AT0476-09 and AT0476-11), compared to GUS expression under control of the 35S promoter (line WS35S:GUS). For each line, 5 replicas were tested. The plants shown have 2 cotyledons and 2 true leaves and were stained for 1 hour (panel a) or were stained overnight (panel b).
Figure 3:
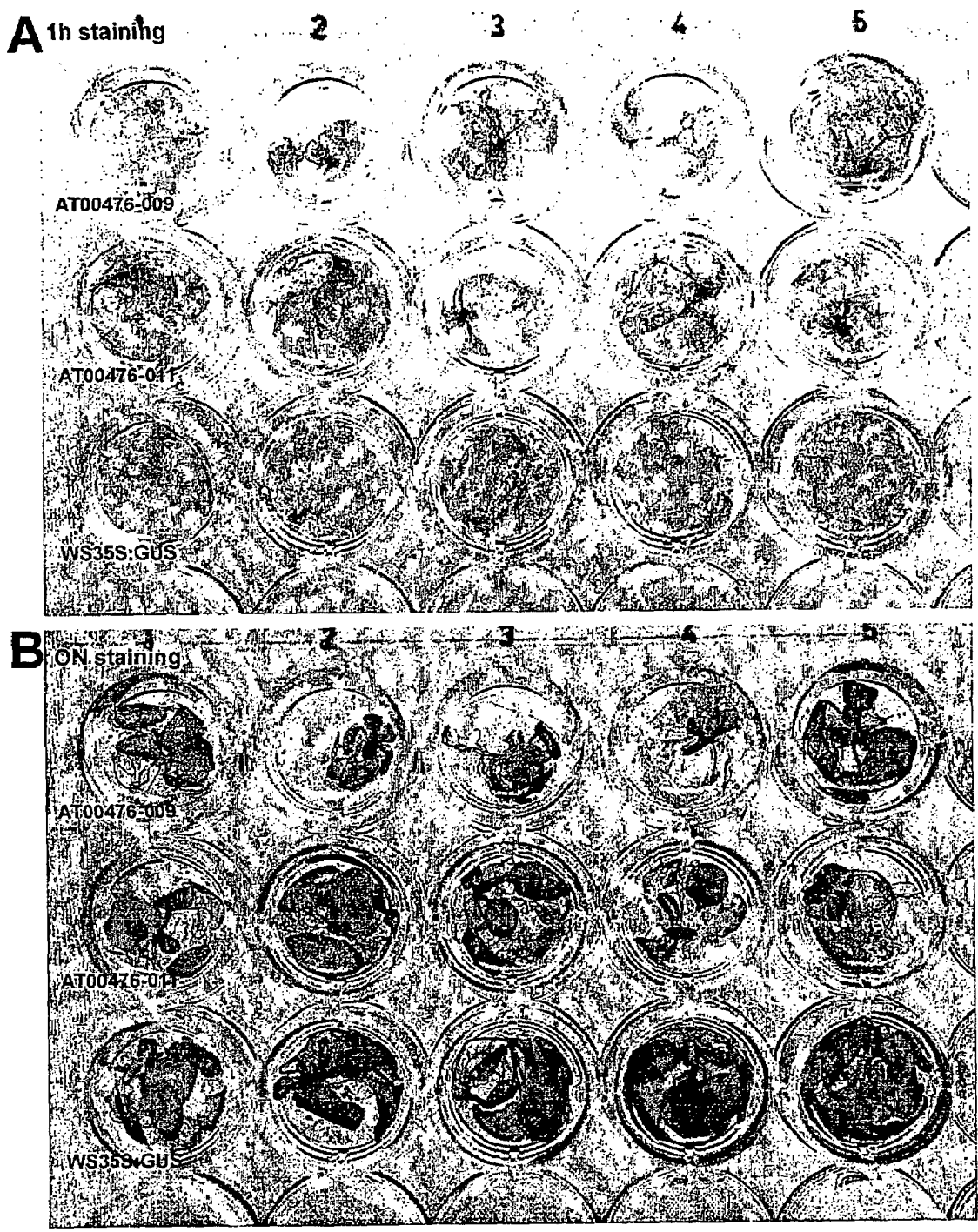
FIG. 3: GUS expression under control of the GOS2 regulatory sequence (lines AT0476-09 and AT0476-11), compared to GUS expression under control of the 35S promoter (line WS35S:GUS). For each line, 5 replicas were tested. The plants shown are in the 10 leaf stage and were stained for 1 hour (panel a) or were stained overnight (panel b).
Figure 4:
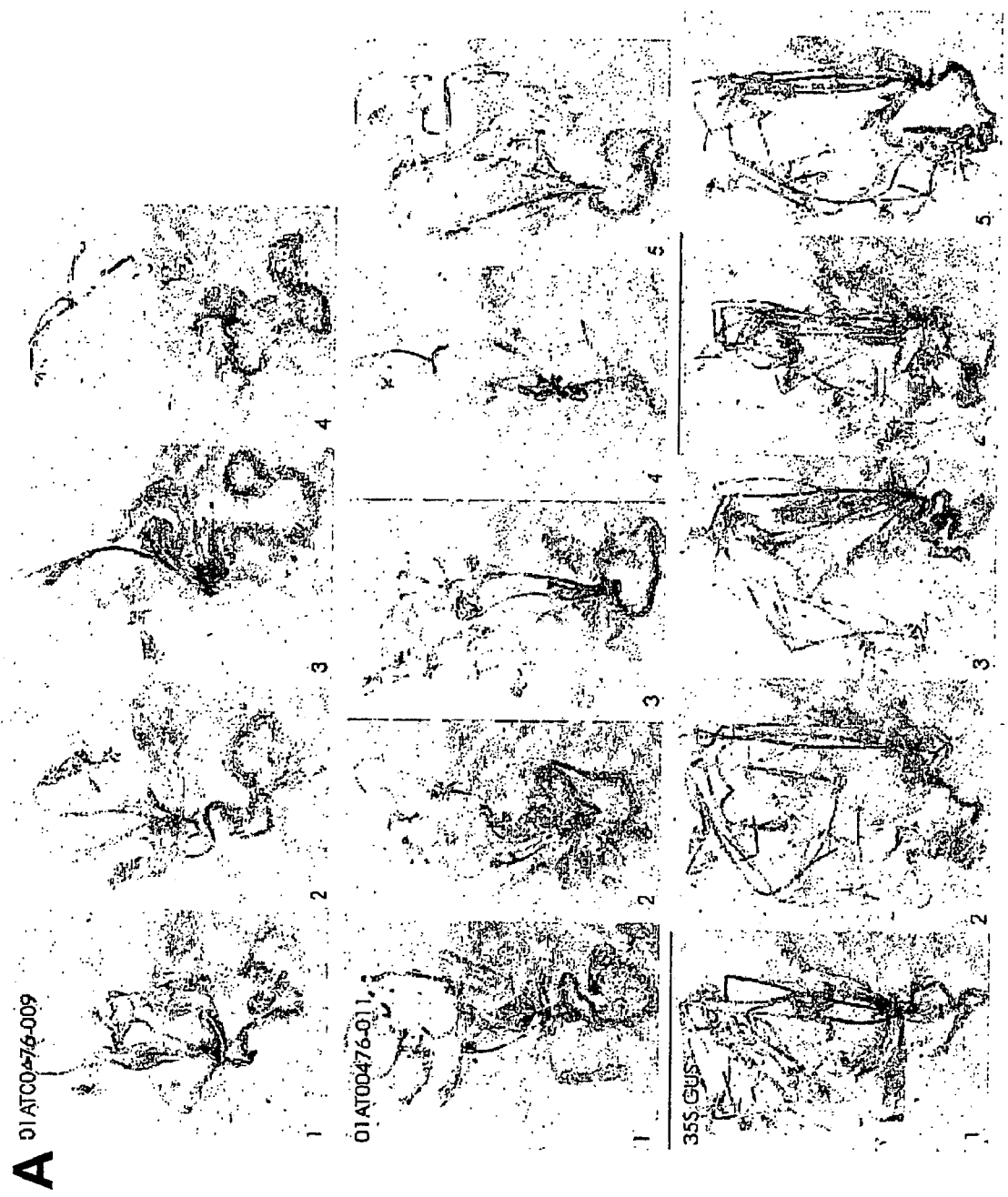
FIG. 4: GUS expression under control of the GOS2 regulatory sequence (lines AT0476-09 and AT0476-11), compared to GUS expression under control of the 35S promoter in line WS35S:GUS. For each line, 5 replicas were tested. The plants shown are in the adult stage with an inflorescence and were stained for 1 hour (panel a) or were stained overnight (panel b).
Figure 4:

For all the plants with the same incubation time during staining (1 hr or overnight), the pattern of GUS expression was similar. The staining of GOS2 plants was as strong as for 35S plants, at all stages that were sampled (2 leaves+2 cotyledons, 10 leaf stage and flowering stage). GOS2 expression appears equally strong and equally constitutive as 35S expression in *Arabidopsis* (FIGS. 2, 3 and 4).

The invention claimed is:

1. A method for expressing in a non-monocotyledonous plant or plant cell a nucleic acid operably linked to a regulatory sequence, wherein said regulatory sequence comprises
SEQ ID NO:1,
said method comprising the introduction of said nucleic acid operably linked to said regulatory sequence into a non-monocotyledonous plant or plant cell, and wherein said regulatory sequence drives expression of said nucleic acid.

2. A method for expressing an endogenous nucleic acid in a non-monocotyledonous plant or plant cell, which method comprises introducing into this plant or plant cell a regulatory sequence comprising
SEQ ID NO:1,
such that the regulatory sequence is operably linked to said endogenous nucleic acid sequence, and wherein said regulatory sequence drives expression of said endogenous nucleic acid.

3. A non-monocotyledonous plant cell comprising or having SEQ ID NO:1 stably integrated into its genome.

4. A non-monocotyledonous plant cell according to claim 3, wherein said non-monocotyledonous plant cell is a fodder or forage legume cell, an ornamental plant cell, a food crop cell, a tree cell or a shrub cell.

5. A plant cell culture, callus or a plant comprising a plant cell according to claim 3.

6. A harvestable part, organ, tissue or transformed propagation material of the plant cell culture, callus or plant according to claim 5.

7. Method for expression of a nucleic acid in a non-monocotyledonous plant or plant cell, said method comprising introducing into said plant or plant cell a regulatory sequence comprising SEQ ID NO 1, wherein said regulatory sequence is operably linked to said nucleic acid which is either an isolated or an endogenous nucleic acid, and wherein said regulatory sequence drives expression of said nucleic acid.

8. A non-monocotyledonous plant cell according to claim 4, wherein said non-monocotyledonous plant cell is a cotton cell, a potato cell, a tomato cell, a cabbage cell, a sugar beet cell, a soybean cell, a bean cell, a sunflower cell or a pea cell.

* * * * *